United States Patent
Wu et al.

(10) Patent No.: US 8,315,352 B2
(45) Date of Patent: Nov. 20, 2012

(54) SYSTEM AND METHOD OF SPECTRAL CALIBRATION AND BASIS MATERIAL DECOMPOSITION FOR X-RAY CT SYSTEMS

(75) Inventors: Xiaoye Wu, Rexford, NY (US); Dan Xu, Schenectady, NY (US); Naveen Chandra, Kenosha, WI (US); Zhanyu Ge, Waukesha, WI (US); Jiang Hsieh, Brookfield, WI (US); Daniel David Harrison, Delanson, NY (US); Mary Sue Kulpins, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/883,631

(22) Filed: Sep. 16, 2010

(65) Prior Publication Data

US 2012/0069952 A1 Mar. 22, 2012

(51) Int. Cl.
*A61B 6/00* (2006.01)
*H05G 1/64* (2006.01)
*G06K 9/00* (2006.01)

(52) U.S. Cl. ............. 378/5; 378/18; 378/98.9; 378/207; 382/130; 382/131

(58) Field of Classification Search ................ 378/5, 18, 378/98.9, 207; 382/130
See application file for complete search history.

(56) References Cited

U.S. PATENT DOCUMENTS

| | | | | |
|---|---|---|---|---|
| 4,571,491 A | * | 2/1986 | Vinegar et al. | 250/252.1 |
| 4,788,706 A | * | 11/1988 | Jacobson | 378/207 |
| 6,748,043 B1 | * | 6/2004 | Dobbs | 378/4 |
| 6,997,610 B2 | * | 2/2006 | Heismann | 378/207 |
| 7,086,780 B2 | | 8/2006 | Wu et al. | |
| 7,149,277 B2 | * | 12/2006 | Tanigawa et al. | 378/18 |
| 7,881,424 B2 | * | 2/2011 | Zhang et al. | 378/5 |
| 7,889,834 B2 | * | 2/2011 | Heismann | 378/4 |
| 2004/0136491 A1 | * | 7/2004 | Iatrou et al. | 378/4 |
| 2004/0228451 A1 | * | 11/2004 | Wu et al. | 378/207 |
| 2005/0259784 A1 | * | 11/2005 | Wu et al. | 378/19 |
| 2006/0159223 A1 | * | 7/2006 | Wu et al. | 378/18 |
| 2009/0161814 A1 | * | 6/2009 | Wu et al. | 378/5 |
| 2010/0014737 A1 | * | 1/2010 | Ruhrnschopf et al. | 382/131 |

OTHER PUBLICATIONS

Xu et al., "Dual Energy CT via Fast kVp Switching Spectrum Estimation," Abstract, SPIE Proceedings Paper, vol. 7258, Medical Imaging 2009: Physics of Medical Imaging, Mar. 13, 2009, pp. 1-10.
Schlomka et al., "Experimental feasibility of multi-energy photon-counting K-edge imaging in pre-clinical computed tomography," Physics in Medicine and Biology, vol. 53, 2008, pp. 4031-4047.

* cited by examiner

*Primary Examiner* — Alexander H Taningco
(74) *Attorney, Agent, or Firm* — Ziolkowski Patent Solutions Group, SC

(57) ABSTRACT

An imaging system includes an x-ray source that emits a beam of x-rays toward an object, a detector that receives high frequency electromagnetic energy attenuated by the object, a data acquisition system (DAS) operably connected to the detector, and a computer operably connected to the DAS. The computer is programmed to compute detector coefficients based on a static low kVp measurement and a static high kVp measurement, capture incident spectra at high and low kVp during fast kVp switching, compute effective X-ray incident spectra at high and low kVp during fast kVp switching using the captured incident spectra, scan a water phantom and normalize the computed detector coefficients to water, adjust the computed effective X-ray incident spectra based on the normalized detector coefficients, compute basis material decomposition functions using the adjusted X-ray incident spectra, and generate one or more basis material density images using the computed basis material decomposition functions.

24 Claims, 5 Drawing Sheets

SYSTEM AND METHOD OF SPECTRAL CALIBRATION AND BASIS MATERIAL DECOMPOSITION FOR X-RAY CT SYSTEMS

BACKGROUND

The present invention relates generally to diagnostic imaging and, more particularly, to a system and method of spectral calibration and basis material decomposition for x-ray CT systems.

Diagnostic devices comprise x-ray systems, magnetic resonance (MR) systems, ultrasound systems, computed tomography (CT) systems, positron emission tomography (PET) systems, ultrasound, nuclear medicine, and other types of imaging systems. Typically, in CT imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry opening within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

In the absence of object scatter, the system derives the behavior at a different energy based on the signal from two regions of photon energy in the spectrum: the low-energy and the high-energy portions of the incident x-ray spectrum. In a given energy region of medical CT, two physical processes dominate the x-ray attenuation: (1) Compton scatter and the (2) photoelectric effect. The detected signals from two energy regions provide sufficient information to resolve the energy dependence of the material being imaged. Furthermore, detected signals from the two energy regions provide sufficient information to determine the relative composition of an object composed of two hypothetical materials.

Thus, a CT imaging system may include an energy discriminating (ED), multi energy (ME), and/or dual energy (DE) CT imaging system. These systems are configured to be responsive to different x-ray spectra. In one example, a conventional third generation CT system may acquire projections sequentially at different peak kilovoltage (kVp) levels, which changes the peak and spectrum of energy of the incident photons comprising the emitted x-ray beams. Two scans are acquired—either (1) back-to-back sequentially in time where the scans require two rotations around the subject, or (2) interleaved as a function of the rotation angle requiring one rotation around the subject, in which the tube operates at, for instance, 80 kVp and 140 kVp potentials. Generally, with the advent of fast-switching generators, back-to-back sequential scanning is preferred, as interleaved imaging data can be mis-registered due to object motion during the imaging session.

A conventional basis material decomposition (BMD) algorithm is based on the concept that, in an energy region for medical CT, the x-ray attenuation of any given material can be represented by a proper density mix of two materials with distinct x-ray attenuation properties, referred to as the basis materials. The BMD algorithm computes two material images that represent the equivalent density of the basis materials based on the measured projections at high and low x-ray photon energy spectra, respectively. By linearly combining the two images, a monochromatic image representation can be formed.

Typically, two or more sets of projection data are typically obtained for an imaged object at different tube peak kilovoltage (kVp) levels, which change the peak and spectrum of energy of the incident photons comprising the emitted x-ray beams or, alternatively, at a single tube peak kilovoltage (kVp) level or spectrum with an energy resolving detector of a detector array. The acquired sets of projection data may be used for BMD. During BMD, the measured projections are converted to a set of density line-integral projections. The density line-integral projections may be reconstructed to form a density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image reveals internal features of an object, expressed in the densities of the two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In addition to a CT number or Hounsfield value, an energy selective CT system can provide additional information related to a material's atomic number and density. This information may be particularly useful for a number of medical clinical applications, where the CT number of different materials may be similar but the atomic number may be quite different. For example, calcified plaque and iodine-contrast enhanced blood may be located together in coronary arteries or other vessels. Calcified plaque and iodine-contrast enhanced blood are known to have distinctly different atomic numbers, but at certain densities these two materials are indistinguishable by CT number alone.

A decomposition algorithm is employable to generate atomic number and density information from energy sensitive x-ray measurements. Multiple energy techniques comprise dual energy, photon counting energy discrimination, dual layered scintillation and/or one or more other techniques designed to measure x-ray attenuation in two or more distinct energy ranges. As an example, any compound or mixture of materials measured with a multiple energy technique may be represented as a hypothetical material having the same x-ray energy attenuation characteristics. This hypothetical material can be assigned an effective atomic number Z. Unlike the atomic number of an element, effective atomic number of a compound is defined by the x-ray attenuation characteristics, and it need not be an integer. This effective Z representation property stems from a well-known fact that x-ray attenuation in the energy range useful for diagnostic x-ray imaging is strongly related to the electron density of compounds, which is also related to the atomic number of materials.

There are various ways to perform material decomposition in dual kVp CT. In one example, a complex phantom is used that contains different materials for a calibration process. In this example, a specially designed phantom is used and the calibration simply inverts a measurement of the material decomposition. However, drawbacks include coverage limitations, cost of the phantom, and calibration time.

In another example, beam spectra are captured and the inversion for material decomposition is performed by modeling the system. Although the method is fast and may be cost effective, the spectra typically have to be precisely aligned or material decomposition can be compromised.

Therefore, it would be desirable to have a system and method of x-ray spectral measurement in fast kVp CT to capture beam spectra with greater accuracy.

BRIEF DESCRIPTION

The present invention is directed to a system and method for spectral calibration and basis material decomposition.

According to an aspect of the present invention, an imaging system includes a high frequency electromagnetic energy source that emits a beam of high frequency electromagnetic energy toward an object to be imaged, a detector that receives high frequency electromagnetic energy emitted by the high frequency electromagnetic energy source and attenuated by the object, a data acquisition system (DAS) operably connected to the detector, and a computer operably connected to the DAS. The computer is programmed to compute detector coefficients based on a static low kVp measurement and a static high kVp measurement, capture incident spectra at high and low kVp during fast kVp switching, compute effective X-ray incident spectra at high and low kVp during fast kVp switching using the captured incident spectra, scan a water phantom and normalize the computed detector coefficients to water, adjust the computed effective X-ray incident spectra based on the normalized detector coefficients, compute basis material decomposition functions using the adjusted X-ray incident spectra, and generate one or more basis material density images using the computed basis material decomposition functions.

According to another aspect of the present invention, a method of imaging includes computing detector coefficients based on a static low kVp measurement and a static high kVp measurement, measuring incident spectral curves at high and low kVp during fast kVp switching, computing effective X-ray incident spectral curves at high and low kVp during fast kVp switching using the captured incident spectral curves, scanning a water phantom and normalizing the computed detector coefficients to water, adjusting the computed effective X-ray incident spectral curves based on the normalized detector coefficients, computing basis material decomposition functions using the adjusted X-ray incident spectral curves, and generating one or more basis material density images using the computed basis material decomposition functions.

According to yet another aspect of the present invention, a non-transitory computer readable medium having stored thereon a computer program which, when executed by a computer, will cause the computer to compute detector coefficients based on a static low energy measurement and a static high energy measurement, capture incident spectra at high and low energy during fast energy switching, compute effective X-ray incident spectra at high and low energy during fast energy switching using the captured incident spectra, scan a water phantom and normalize the computed detector coefficients to water, adjust the computed effective X-ray incident spectra based on the normalized detector coefficients, compute basis material decomposition functions using the adjusted X-ray incident spectra, and generate one or more basis material density images using the computed basis material decomposition functions.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION

Diagnostics devices comprise x-ray systems, magnetic resonance (MR) systems, ultrasound systems, computed tomography (CT) systems, positron emission tomography (PET) systems, ultrasound, nuclear medicine, and other types of imaging systems. Applications of x-ray sources comprise imaging, medical, security, and industrial inspection applications. However, it will be appreciated by those skilled in the art that an implementation is applicable for use with single-slice or other multi-slice configurations. Moreover, an implementation is employable for the detection and conversion of x-rays. However, one skilled in the art will further appreciate that an implementation is employable for the detection and conversion of other high frequency electromagnetic energy. An implementation is employable with a "third generation" CT scanner and/or other CT systems.

The operating environment of the present invention is described with respect to a sixty-four-slice computed tomography (CT) system. However, it will be appreciated by those skilled in the art that the present invention is equally applicable for use with other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
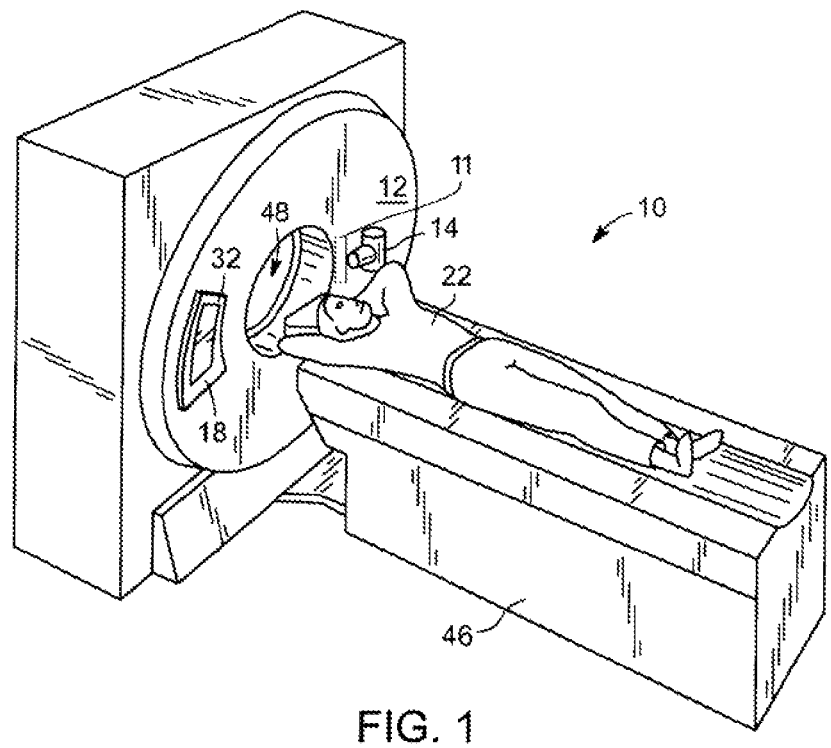
FIG. 1 is a pictorial view of a CT imaging system.
Figure 2:
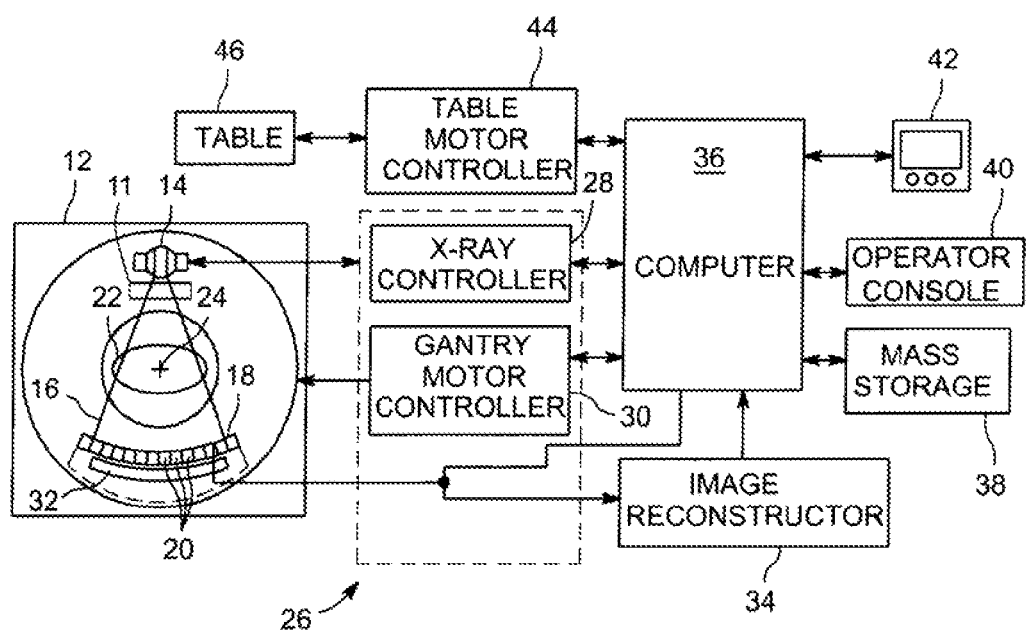
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
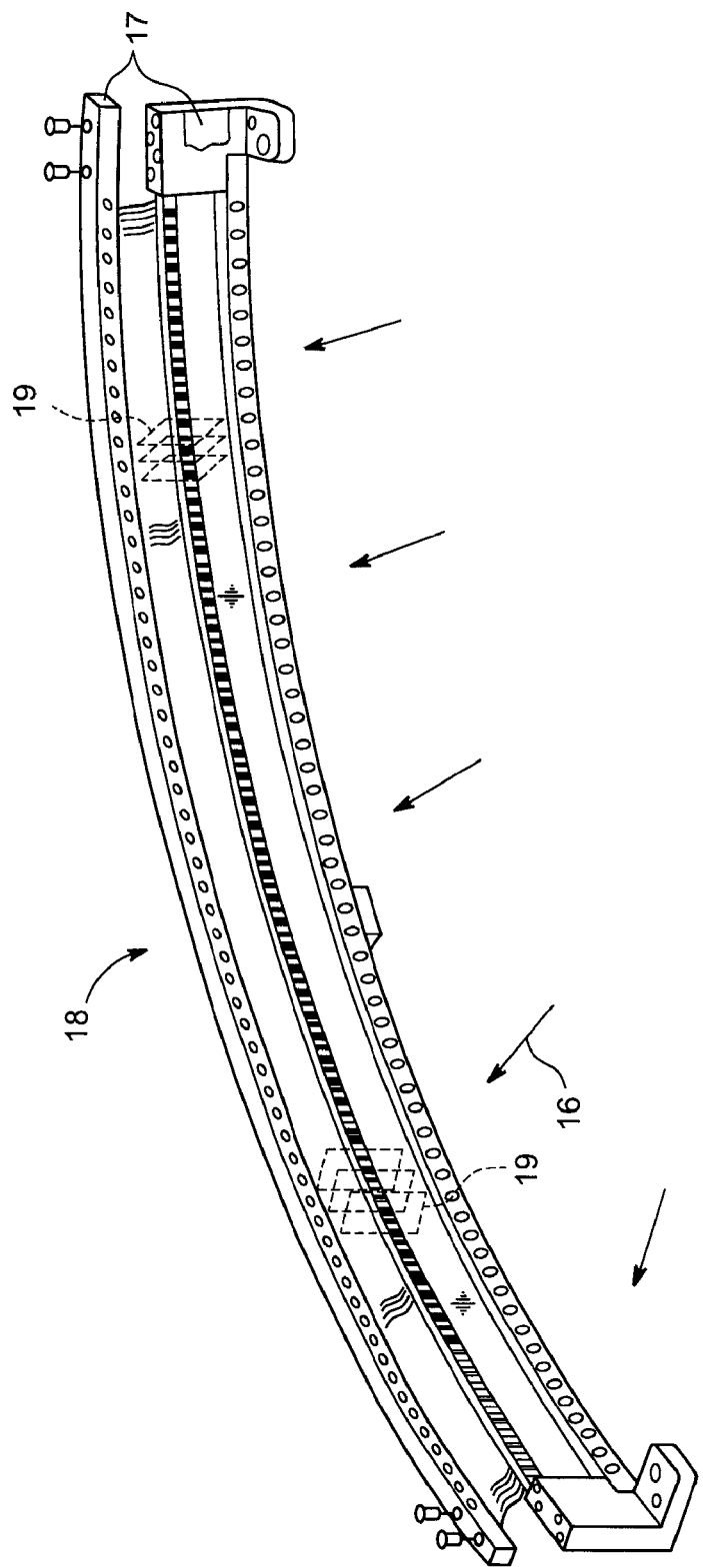
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
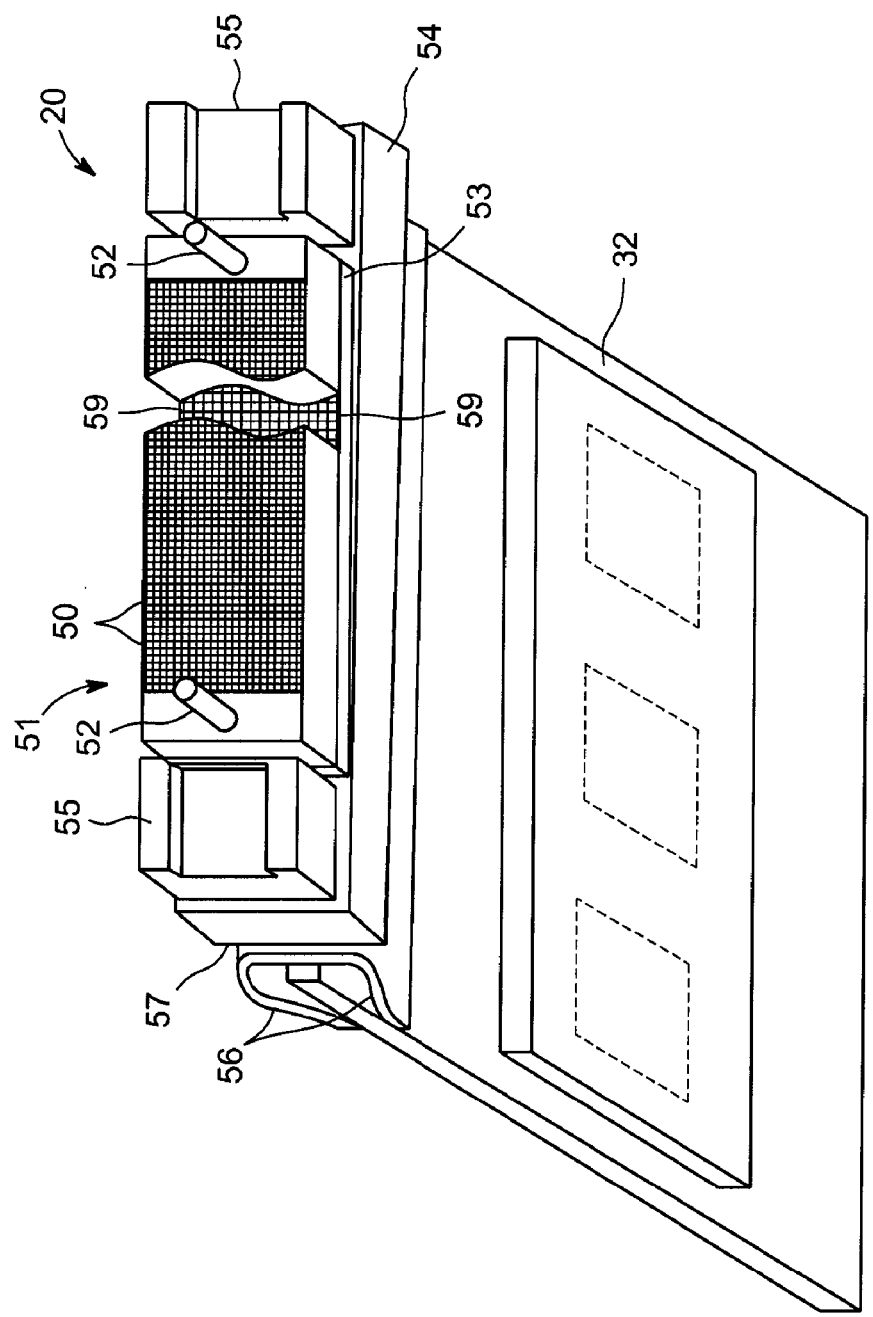
FIG. 4 is a perspective view of one embodiment of a CT detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

As described above, each detector 20 may be designed to directly convert radiographic energy to electrical signals containing energy discriminatory or photon count data. In a preferred embodiment, each detector 20 includes a semiconductor layer fabricated from CZT. Each detector 20 also includes a plurality of metalized anodes attached to the semiconductor layer. Such detectors 20 may include an electrical circuit having multiple comparators thereon which may reduce statistical error due to pileup of multiple energy events.

Referring back to FIGS. 1 and 2, an illustrative discussion is now presented in connection with an implementation of a decomposition algorithm. An image or slice is computed which may incorporate, in certain modes, less or more than 360 degrees of projection data to formulate an image. The image may be collimated to desired dimensions using blades or plates 19 of FIG. 3 in front of the x-ray source and different detector apertures. A collimator typically defines the size and shape of the beam of x-rays 16 that emerges from the x-ray source 14, and a bowtie filter 11 may be included in the system 10 to further control the dose to the patient 22. A typical bowtie filter 11 attenuates the beam of x-rays 16 to accommodate the body part being imaged, such as head or torso, such that, in general, less attenuation is provided for x-rays passing through or near an isocenter of the patient 22. The bowtie filter 11 shapes the x-ray intensity during imaging in accordance with the region-of-interest (ROI), field of view (FOV), and/or target region of the patient 22 being imaged.

As the x-ray source 14 and the detector array 18 rotate, the detector array 18 collects data of the attenuated x-ray beams. The data collected by the detector array 18 undergoes pre-processing and calibration to condition the data to represent the line integrals of the attenuation coefficients of the scanned object or the patient 22. The processed data are commonly called projections.

Figure 5:
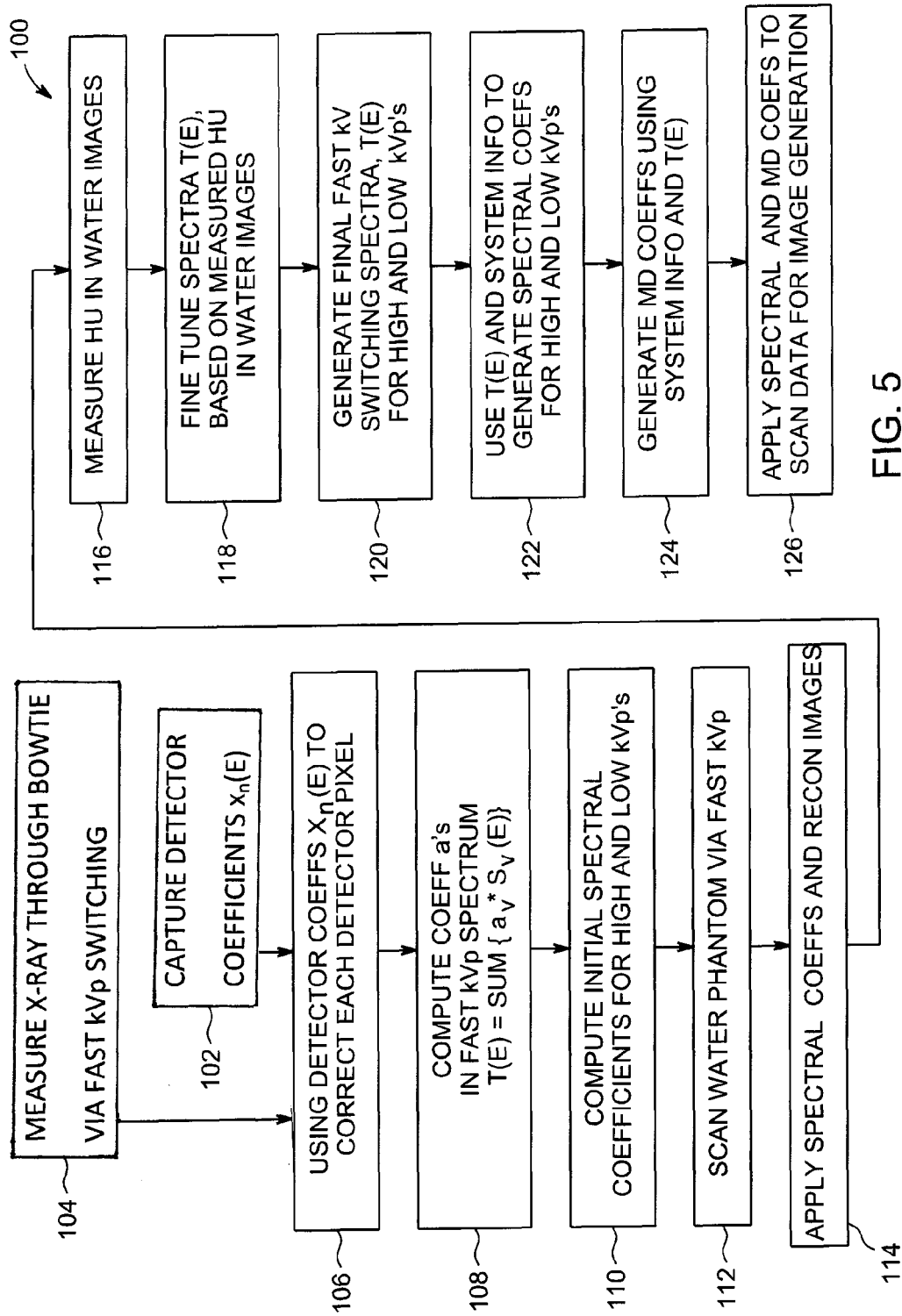
FIG. 5 illustrates a technique for may be calibrating a system for basis material decomposition according to embodiments of the invention.

System 10 illustrated in FIGS. 1-4 may be calibrated for basis material decomposition according to embodiments of the invention. The steps of spectral calibration and the capture of material decomposition functions are described in the following and with respect to FIG. 5. Technique 100 begins at step 102 by executing sections 1) through 3) below to capture detector coefficients $X_n(E)$ in a static kVp environment.

1) Compute Incident X-Ray Spectrum at a Static kVp

Spectra at several kVps are first computed using existing simulation software for X-ray production under a given target material, anode angle, beam filter configuration. Typically, the tube voltages (kVp) are set at 70, 80, 100, 120, 140 and 150 kVp for systems that operate between 80 and 140 kVp.

Corresponding relative X-ray photon production as a function of energy is expressed as, $S_k(E)$, where E is the photon energy, k is a peak voltage value.

2) Fine-Adjust the Computed X-Ray Spectrum at a Static kVp

Assume the bowtie is made of several materials, each of which is precisely machined and placed to a known thickness $L_m(i)$ seen by detector i, where m is the bowtie material index, with a density of $D_m$ with associated X-ray attenuation coefficients $\mu_m(E)$. At a tube voltage kVp, air signal is measured with and without the bowtie at the same mA setting. The measurement is averaged over enough views to remove statistical noise. The averaged values are noted as $A_k(i)$ and $B_k(i)$, respectively for measurements without and with a bowtie.

At the same kVp, the tube spectrum $T_k(E)$ in a CT system might not be the same as the computed spectrum $S_v(E)$. In this method, $T_k(E)$ is estimated as a weighted sum of several computed spectra:

$$T_k(E) = \sum_v a_v(k) S_v(E).$$ Eqn. 1

By equating the computed and measured projection ratios without and with the bowtie, $$\frac{\sum_E T_k(E)E}{\sum_E T_k(E)E e^{-\Sigma_m L_m(i) D_m \mu_m(E)}} = \frac{A_k(i)}{B_k(i)},$$ Eqn. 2 where the extra factor E accounts for the energy-integrating nature of the detection system. Substituting Eqn. 1 to Eqn. 2:

$$\frac{\sum_E \left( \sum_v a_v(k) S_v(E) E \right)}{\sum_E \left( \sum_v a_v(k) S_v(E) E e^{-\Sigma_m L_m(i) D_m \mu_m(E)} \right)} = \frac{A_k(i)}{B_k(i)}.$$ Eqn. 3

Fitting data in Eqn. 3 along an X-ray fan direction (x-direction) detector channel i, parameters $a_v(k)$ can be computed, resulting in a more accurate capture of an incident X-ray spectrum for the CT system. This process may be performed for all the kVps at which the CT system is capable of scanning.

3) Perform Air Scans at a Number of Static kVps and Capture Detection Coefficients of the System A number of kVp bowtie scans are measured to capture the detection efficiency as a function of the incident photon energy for each individual detector channel. In a CT system, where typically, four kVps are offered, bowtie scans are measured and averaged for the four kVps, resulting in the following normalized projection data set, $N_k(i)$, where k is the kVp value, i is the detector channel along X-ray fan direction, and, $$N_k(i) = \frac{B_k(i)}{\sum_i B_k(i)}.$$ Eqn. 4

Note: the detector efficiency of channel i is defined as f(E,i):

$$\frac{\sum_E T_k(E) E f(E, i) e^{-\Sigma_m L_m(i) D_m \mu_m(E)}}{\sum_i \left( \sum_E T_k(E) E f(E, i) e^{-\Sigma_m L_m(i) D_m \mu_m(E)} \right)} = N_k(i).$$ Eqn. 5

In a CT system, the detection efficiency can be expressed as:

$$f(E,i) = \epsilon(E,i)(1 - e^{-b_s(E) * \mu_s(E)})$$ Eqn. 6, where, $b_s(E)$ and $\mu_s(E)$ are mass-thickness product and X-ray attenuation coefficients of the scintillator, $\epsilon(E,i)$ is the detector channels to channel detection efficiency, and is typically very close to unity. Let the detector stopping power $(1 - e^{-L_s * \mu_s(E)}) = \delta(E)$, By expressing $\epsilon(E,i)$ in N term polynomial, $$\epsilon(E, i) = \sum_0^{N-1} X_n(i) E^n.$$ Eqn. 7

Eqn. 5 can be approximated as:

$$\frac{\sum_E \left( T_k(E) E \delta(E) e^{-\Sigma_m L_m(i) D_m \mu_m(E)} \sum_0^{N-1} X_n(i) E^n \right)}{\sum_i \left( \sum_E T_k(E) E \delta(E, i) e^{-\Sigma_m L_m(i) D_m \mu_m(E)} \right)} \approx N_k(i),$$ Eqn. 8.

By simplification, equation (8) can be expressed:

$$\frac{\sum_0^{N-1} X_n(i) P_k(E, i)}{R_k(E, i)} \approx N_k(i),$$ Eqn. 9, where, $$P_k(E, i) = \sum_{n=0}^{N-1} X_n(i) \sum_E E^n T_k(E) E \delta(E) e^{-\Sigma_m L_m(i) D_m \mu_m(E)},$$

and $$R_k(E, i) = \sum_E E^n T_k(E) E \delta(E) e^{-\Sigma_m L_m(i) D_m \mu_m(E)}.$$

With the number of kVp measurements $N_k(i)$ greater than or equal to the number of terms N in Eqn. 7, parameters $X_n(i)$ can be obtained channel by channel through linear fitting of Eqn. 9 to capture detection efficiency function $\epsilon(E,i)$.

Thus, technique 100 includes step 102 by executing sections 1) through 3) above to capture detector coefficients $X_n(E)$ in a static kVp environment. And, although the steps performed in sections 1) through 3) are to fine-tune the X-ray spectrum by matching the bowtie measurements, typically the x-ray spectrum produced at a static kVp can instead be computed through simulation.

In a system where the kVp is switched rapidly between a high kVp and a low kVp setting, the effective spectrum at the low and the high kVp periods may be different from that of a static kVp, because switching time from one kVp to the other can be not neglected compared to a CT projection view time. The method described in Section 2 may be effective when applied to capture the effective incident spectra at high and low kVp setting separately. However, because of the aforementioned switching time, the steps of spectral calibration include accounting for dynamic affects as well, according to the invention.

Thus, referring back to technique 100, at step 104 air scans without and with bowtie are measured in parallel with step 102. Views corresponding to high and low kVp settings are separated and averaged accordingly. The technique in section 2 is applied to high and low setting independently to obtain the effective spectra expressed in the weighted sum of the computed kVp spectra, and detector coefficients $X_n(E)$ may be used to correct each detector pixel at step 106.

At step 108 the weighting coefficients are captured, resulting in the following effective X-ray incident spectra at low and high kVp settings, $$T_{low}(E) = \sum_v a_{v,low}(k)S_v(E)$$

$$T_{high}(E) = \sum_v a_{v,high}(k)S_v(E).$$

Eqn. 10

With a spectrum T(E) (switching kVp or static kVp) and detection efficiency, the conventional spectral calibration coefficients that normalizes water to its target CT number (typically, water CT number=1000, and air=0) can be achieved as the following. Referring still to technique 100, step 110 includes computing initial spectral calibration coefficients for high and low kVps.

The projection values (after negative log) through various thicknesses of water can be computed (not measured) as, $$p_w(L_w, i) = -\log\left(\frac{\sum_E T(E)Ef(E, i)e^{-\sum_m L_m(i)D_m\mu_m(E) - L_w\mu_w(E)}}{\sum_E T(E)Ef(E, i)e^{-\sum_m L_m(i)D_m\mu_m(E)}}\right).$$

Eqn. 11 where, $L_w$ is the water thickness, $\mu_w(E)$ is the water X-ray mass attenuation coefficient. By computing $p_w(L_w,i)$ with $L_w$ ranging from zero to a largest penetration accounted for by the system at an interval small enough (i.e., 0.5 cm), data pair sets $(L_w, p_w(L_w, i))$ are established for detector channel i. The spectral calibration function $f_{cal,i}()$ is defined as $\mu L_w = f_{cal,i}(p_w(L_w, i))$, where parameter $\mu$ is a scaling constant (that can be artificially set) and is self-normalized during the image reconstruction process.

In a CT system, this function is often expressed as a $M^{th}$ order of polynomial, with M typically equals to 3 or 4, and:

$$\mu L_w = \sum_{r=1}^{r=M} c_r(i) p_w(L_w, i)^r.$$

Eqn. 12 where, coefficients $c_r(i)$ can be captured by fitting equation (12) with the data pair sets $(L_w, p_w(L_w, i))$.

Calibration coefficients may be adjusted with a water phantom measurement. To further improve the accuracy of the calibration accuracy, a water phantom is scanned at step 112, the computed spectral coefficients from step 110 are applied to reconstructed images at step 114, and the average Hounsfield Units (HU) or CT number "V" in a region of interest is measured in the reconstructed image at step 116. A linear scaling factor 1000.0/V is applied to the calibration coefficients across all the detector channels, $$C_r(i) = \frac{1000.0}{V} c_r(i)$$

where, $C_r(i)$ is the improved calibration coefficients, assuming the target CT number for water is 1000.

At step 118 the spectra T(E) are fined tuned based on measured HU are fine tuned based on the measured HU of step 116. At step 120, based on measured V value above, the spectra in Eqn. 10 of both high and low kVp can be fine adjusted to yield better accuracy for precise MD decomposition. The adjustment to the spectra can be achieved by at least two methods:
Method A: fine adjust the system parameter, such as the bowtie material density to iterate the process until V=1000.0 for both high and low kVp.
Method B: empirically shape $T_{low0}$ and $T_{high}$ with an attenuation of positive or negative length of a selected material, and regenerate images in section 5, until V=1000.0. This process may increase the MD accuracy, even though the spectra may only be mildly altered with this process.

At step 122 $T_{low}(E)$, $T_{high}(E)$, and system information may be used to generate corresponding spectral coefficients for high and low kVps. At step 124 material density coefficients may be generated, as understood in the art, using system information and T(E) values.

As known in the art, in dual kVp switching scans, two projections at the same ray path are measured at high and low kVp settings, respectively. A basis material decomposition method is then applied to obtain density line integrals of the two chosen basis material, $m_1$ and $m_2$. With the obtained CT system parameters, spectra ($T_{low}(E)$, $T_{high}(E)$) and detection efficiency function $f(E,i)$, the basis material decomposition function can be established as shown in the following.

First, compute data pairs $((L_{m1},L_{m2}),(P_{low}(i),P_{high}(i))$. The computed (not measured) projections at high and low kVp settings are, $$p_{low}(i) = -\log\left(\frac{\sum_E T_{low}(E)Ef(E, i)e^{-\sum_m L_m(i)D_m\mu_m(E) - L_{m1}\mu_{m1}(E) - L_{m2}\mu_{m2}(E)}}{\sum_E T_{low}(E)Ef(E, i)e^{-\sum_m L_m(i)D_m\mu_m(E)}}\right)$$

$$p_{high}(i) = -\log\left(\frac{\sum_E T_{high}(E)Ef(E, i)e^{-\sum_m L_m(i)D_m\mu_m(E) - L_{m1}\mu_{m1}(E) - L_{m2}\mu_{m2}(E)}}{\sum_E T_{high}(E)Ef(E, i)e^{-\sum_m L_m(i)D_m\mu_m(E)}}\right),$$

Eqn. 13, and the corresponding spectrally corrected projections are, $$P_{low}(i) = \sum_{r=1}^{r=M} C_r(i) p_{low}(i)^r,$$

$$P_{high}(i) = \sum_{r=1}^{r=M} C_r(i) p_{high}(i)^r.$$

Eqn. 14

Second, the basis material decomposition functions are calculated. With the data pairs for various basis material thicknesses, the basis material functions can be expressed as, $$L_{m1} = f_{1,i}(P_{low}(i), P_{high}(i))$$

$$L_{m2} = f_{2,i}(P_{low}(i), P_{high}(i)),$$

Eqn. 15, where, decomposition functional forms $f_{1,i}$ and $f_{2,i}$ are often expressed as polynomials at R and S orders for low and high kVp projections, respectively:

$$f_{1,i}(P_{low}(i), P_{high}(i)) = \sum_{r=1}^{R}\sum_{s=1}^{S} M_1(r,s) P_{low}(i)^r P_{high}(i)^s,$$ Eqn. 16

$$f_{2,i}(P_{low}(i), P_{high}(i)) = \sum_{r=1}^{R}\sum_{s=1}^{S} M_2(r,s) P_{low}(i)^r P_{high}(i)^s.$$

Decomposition coefficients $M_2(r,s)$ and $M_2(r,s)$ can be obtained through fitting computed data pairs (($L_{m1}$, $L_{m2}$), ($P_{low}(i), P_{high}(i)$)). It should be noted that similar decomposition coefficients could also be obtained for data pairs (($L_{m1}$, $L_{m2}$),($p_{low}(i), p_{high}(i)$)) without spectral correction, if the data flow is to derive material density integrals without spectral correction on the projection data.

At step 126, spectral and material decomposition coefficients may be applied to acquired scan data for image generation. During a switching dual kVp scan, the measured projections (not computed) at high and low kVp settings are separated, pre-processed and view aligned to yield dual kVp projection pairs ($p\_m_{low}(i), p\_m_{high}(i)$) at a given view angle, the same ray path for detector channel i. These projection pairs are further processed to obtain spectrally corrected projections ($P\_M_{low}(i)$ $P\_M_{high}(i)$) and basis material decomposed density integrals ($\int D_{m1}dl, \int D_{m2}dl$), using the coefficients obtained in the calibration process described above, yielding the following sets of Eqns. 17 and 18:

$$P\_M_{low}(i) = \sum_{r=1}^{r=M} C_r(i) p\_m_{low}(i)^r$$ Eqn. 17

$$P\_M_{high}(i) = \sum_{r=1}^{r=M} C_r(i) p\_m_{high}(i)^r.$$

$$\int D_{m1}dl = \sum_{r=1}^{R}\sum_{s=1}^{S} M_1(r,s) P\_M_{low}(i)^r P\_M_{high}(i)^s$$ Eqn. 18

$$\int D_{m2}dl = \sum_{r=1}^{R}\sum_{s=1}^{S} M_2(r,s) P\_M_{low}(i)^r P\_M_{high}(i)^s.$$

The low and high kVp, basis materials density images can be obtained by reconstructing projection data in Eqns. 17 and 18, respectively.

Overall, it should be noted that, though the above methods uses dual kVp as an example, it can be effectively applied to systems switching among three or more kVp settings.

Figure 6:
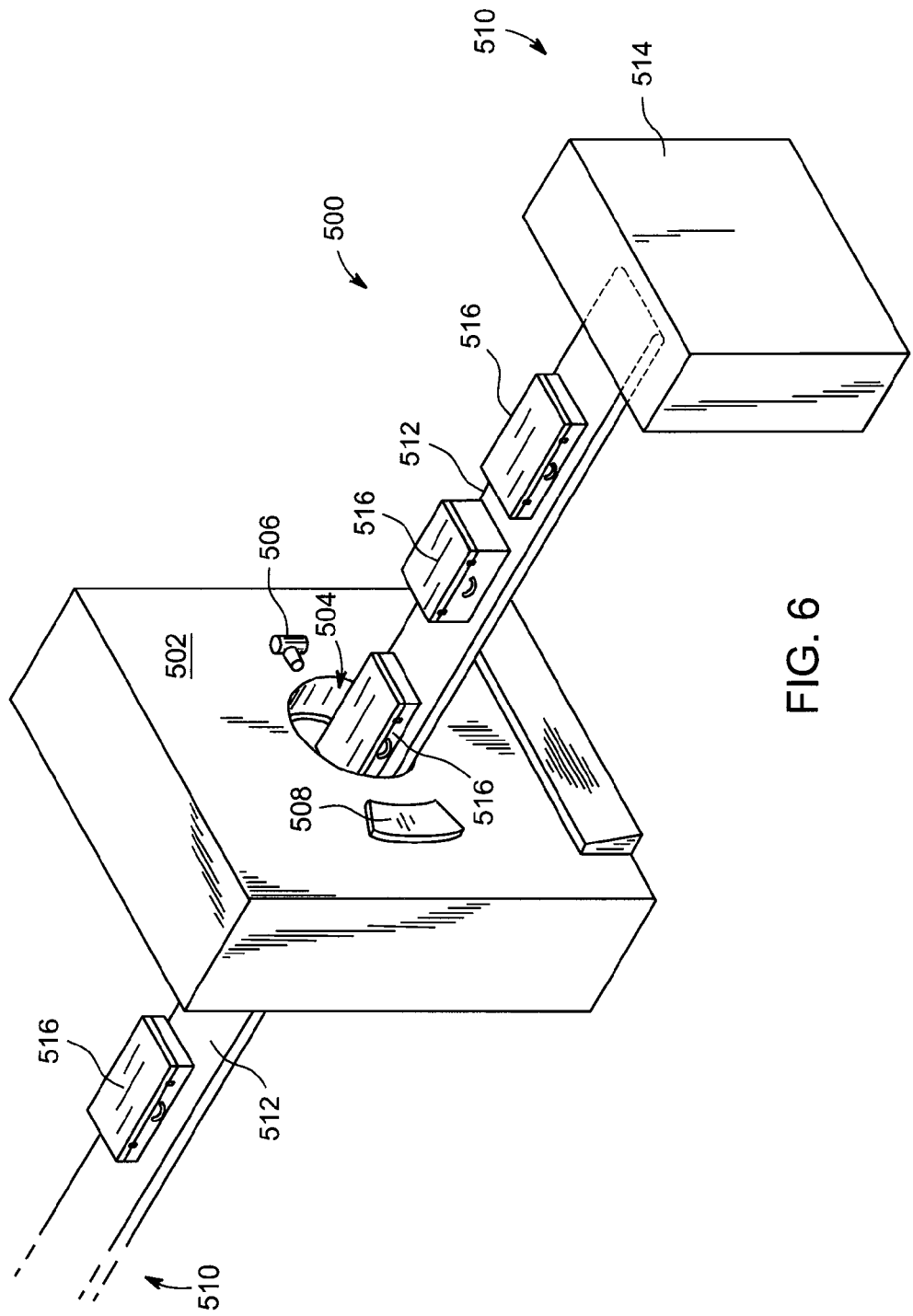
FIG. 6 is a pictorial view of a CT system for use with a non-invasive package inspection system.

Referring now to FIG. 6, package/baggage inspection system 500 includes a rotatable gantry 502 having an opening 504 therein through which packages or pieces of baggage may pass. The rotatable gantry 502 houses an x-ray and/or high frequency electromagnetic energy source 506 as well as a detector assembly 508 having scintillator arrays comprised of scintillator cells. A conveyor system 510 is also provided and includes a conveyor belt 512 supported by structure 514 to automatically and continuously pass packages or baggage pieces 516 through opening 504 to be scanned. Objects 516 are fed through opening 504 by conveyor belt 512, imaging data is then acquired, and the conveyor belt 512 removes the packages 516 from opening 504 in a controlled and continuous manner. As a result, postal inspectors, baggage handlers, and other security personnel may non-invasively inspect the contents of packages 516 for explosives, knives, guns, contraband, etc. An exemplary implementation can aid in the development of automatic inspection techniques, such as explosive detection in luggage.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Therefore, according to an embodiment of the present invention, an imaging system includes a high frequency electromagnetic energy source that emits a beam of high frequency electromagnetic energy toward an object to be imaged, a detector that receives high frequency electromagnetic energy emitted by the high frequency electromagnetic energy source and attenuated by the object, a data acquisition system (DAS) operably connected to the detector, and a computer operably connected to the DAS. The computer is programmed to compute detector coefficients based on a static low kVp measurement and a static high kVp measurement, capture incident spectra at high and low kVp during fast kVp switching, compute effective X-ray incident spectra at high and low kVp during fast kVp switching using the captured incident spectra, scan a water phantom and normalize the computed detector coefficients to water, adjust the computed effective X-ray incident spectra based on the normalized detector coefficients, compute basis material decomposition functions using the adjusted X-ray incident spectra, and generate one or more basis material density images using the computed basis material decomposition functions.

According to another embodiment of the present invention, a method of imaging includes computing detector coefficients based on a static low kVp measurement and a static high kVp measurement, measuring incident spectral curves at high and low kVp during fast kVp switching, computing effective X-ray incident spectral curves at high and low kVp during fast kVp switching using the captured incident spectral curves, scanning a water phantom and normalizing the computed detector coefficients to water, adjusting the computed effective X-ray incident spectral curves based on the normalized detector coefficients, computing basis material decomposition functions using the adjusted X-ray incident spectral curves, and generating one or more basis material density images using the computed basis material decomposition functions.

According to yet another embodiment of the present invention, a non-transitory computer readable medium having stored thereon a computer program which, when executed by a computer, will cause the computer to compute detector coefficients based on a static low energy measurement and a static high energy measurement, capture incident spectra at high and low energy during fast energy switching, compute effective X-ray incident spectra at high and low energy during fast energy switching using the captured incident spectra, scan a water phantom and normalize the computed detector coefficients to water, adjust the computed effective X-ray incident spectra based on the normalized detector coefficients, compute basis material decomposition functions using the adjusted X-ray incident spectra, and generate one or more basis material density images using the computed basis material decomposition functions.

The present invention has been described in terms of the preferred embodiment, and it is recognized that equivalents, alternatives, and modifications, aside from those expressly stated, are possible and within the scope of the appending claims.

What is claimed is:

1. An imaging system comprising:
    a high frequency electromagnetic energy source that emits a beam of high frequency electromagnetic energy toward an object to be imaged;
    a detector that receives high frequency electromagnetic energy emitted by the high frequency electromagnetic energy source and attenuated by the object;
    a data acquisition system (DAS) operably connected to the detector; and
    a computer operably connected to the DAS and programmed to:
        compute detector coefficients based on a static low kVp measurement and a static high kVp measurement;
        capture incident spectra at high and low kVp;
        compute effective X-ray incident spectra at high and low kVp using the captured incident spectra;
        scan a water phantom and normalize the computed detector coefficients to water;
        adjust the computed effective X-ray incident spectra based on the normalized detector coefficients;
        compute basis material decomposition functions using the adjusted X-ray incident spectra; and
        generate one or more basis material density images using the computed basis material decomposition functions.

2. The imaging system of claim 1 wherein the computer is programmed to:
    compute the effective X-ray incident spectra using measured projections obtained with and without a bowtie filter position between the high frequency electromagnetic energy source and the detector; and
    compute the effective X-ray incident spectra using weighting coefficients that are derived from the measured projections.

3. The imaging system of claim 1 wherein the computer is programmed to normalize the computed detector coefficients to water by computing projections through a plurality of thicknesses of water, wherein the computer is programmed to normalize the computed detector coefficients to water by calculating a spectral calibration function that enables a curvefit using the computed projections through the plurality of thicknesses of water.

4. The imaging system of claim 3 wherein the computer is programmed to scan a water phantom and adjust the computed detector coefficients based thereon.

5. The imaging system of claim 1 wherein the computer is programmed to adjust the computed effective X-ray incident spectra by adjusting a bowtie material density that is used to compute the effective X-ray incident spectra.

6. The imaging system of claim 1 wherein the computer is programmed to adjust the computed effective X-ray incident spectra by including an additional selected material positioned between the high frequency electromagnetic energy source and the detector, and adjust the computed effective X-ray incident spectra by including in the computation that the additional selected material has one of a positive and a negative attenuation coefficient.

7. The imaging system of claim 1 wherein the computer is programmed to capture the incident spectra at high and low kVp during fast kVp switching, wherein the fast kVp switching is defined as back-to-back sequential scanning.

8. The imaging system of claim 1 wherein the computer is programmed to compute the detector coefficients by being further programmed to:
    1) compute an incident static X-ray spectrum at the low kVp and at the high kVp using simulation software;
    2) measure averaged air signal over one or more views with and without a bowtie filter and with a constant mA; and
    compute the detector coefficients based at least on 1) and 2).

9. A method of imaging comprising:
    computing detector coefficients based on a static low kVp measurement and a static high kVp measurement;
    measuring incident spectral curves at high and low kVp;
    computing effective X-ray incident spectral curves at high and low kVp using the captured incident spectral curves;
    scanning a water phantom and normalizing the computed detector coefficients to water;
    adjusting the computed effective X-ray incident spectral curves based on the normalized detector coefficients;
    computing basis material decomposition functions using the adjusted X-ray incident spectral curves; and
    generating one or more basis material density images using the computed basis material decomposition functions.

10. The method of claim 9 comprising:
    computing the effective X-ray incident spectral curves using measured projections obtained with and without a bowtie filter position between the high frequency electromagnetic energy source and the detector; and
    computing the effective X-ray incident spectral curves using weighting coefficients that are derived from the measured projections.

11. The method of claim 9 comprising normalizing the computed detector coefficients to water by calculating a spectral calibration function that enables a curvefit using the computed projections through the plurality of thicknesses of water; and normalizing the computed detector coefficients to water by calculating a spectral calibration function that enables a curvefit using the computed projections through the plurality of thicknesses of water.

12. The method of claim 11 comprising scanning a water phantom and adjusting the computed detector coefficients based thereon.

13. The method of claim 9 comprising adjusting the computed effective X-ray incident spectral curves by adjusting a bowtie material density that is used to compute the effective X-ray incident spectra curves.

14. The method of claim 9 comprising adjusting the computed effective X-ray incident spectral curves by including an additional selected material positioned between the high frequency electromagnetic energy source and the detector, and adjusting the computed effective X-ray incident spectral curves by including the additional selected material to have one of a positive and a negative attenuation coefficient.

15. The method of claim 9 wherein measuring the incident spectral curves at high and low kVp comprises measuring the incident spectral curves at high and low kVp during fast kVp switching, and wherein fast kVp switching comprises back-to-back sequential scanning.

16. The method of claim 9 wherein computing the detector coefficients comprises:
   computing X-ray spectra under a given target material, anode angle and beam filter at different kVps;
   measuring, with and without a bowtie filter, incident spectra over two or more views;
   equating ratios of the computed spectra and the measured spectra; and
   computing the detector coefficients based on the equated ratios.

17. A non-transitory computer readable medium having stored thereon a computer program which, when executed by a computer, will cause the computer to:
   compute detector coefficients based on a static low energy measurement and a static high energy measurement;
   capture incident spectra at high and low energy;
   compute effective X-ray incident spectra at high and low energy using the captured incident spectra;
   scan a water phantom and normalize the computed detector coefficients to water;
   adjust the computed effective X-ray incident spectra based on the normalized detector coefficients;
   compute basis material decomposition functions using the adjusted X-ray incident spectra; and
   generate one or more basis material density images using the computed basis material decomposition functions.

18. The computer readable medium of claim 17 wherein the computer program stored thereon causes the computer to:
   compute the effective X-ray incident spectra using measured projections obtained with and without a bowtie filter position between the high frequency electromagnetic energy source and the detector; and
   compute the effective X-ray incident spectra using weighting coefficients that are derived from the measured projections.

19. The computer readable medium of claim 17 wherein the computer program stored thereon causes the computer to normalize the computed detector coefficients to water by computing projections through a plurality of thicknesses of water, and to normalize the computed detector coefficients to water by calculating a spectral calibration function that enables a curvefit using the computed projections through the plurality of thicknesses of water.

20. The computer readable medium of claim 19 wherein the computer program stored thereon causes the computer to scan a water phantom and adjust the computed detector coefficients based thereon.

21. The computer readable medium of claim 17 wherein the computer program stored thereon causes the computer to adjust the computed effective X-ray incident spectra by being programmed to adjust a bowtie material density that is used to compute the computed effective X-ray incident spectra.

22. The computer readable medium of claim 17 wherein the computer program stored thereon causes the computer to adjust the computed effective X-ray incident spectra by including an additional selected material positioned between the high frequency electromagnetic energy source and the detector, and adjust the computed effective X-ray incident spectra by including the additional selected material to have one of a positive and a negative attenuation coefficient.

23. The computer readable medium of claim 17 wherein the computer program stored thereon causes the computer to capture the incident spectra at high and low energy during fast energy switching, and wherein the fast energy switching comprises back-to-back sequential scanning.

24. The computer readable storage medium of claim 17 wherein the computer program stored thereon causes the computer to:
   simulate spectra at more than one x-ray energy;
   obtain measured spectra at more than one energy;
   calculate a first ratio of the simulated spectra at two energies, and a second ratio of the measured spectra at the two energies; and
   compute the detector coefficients based on the first ratio and the second ratio.

* * * * *